US011655218B2

(12) United States Patent
Fujiwara

(10) Patent No.: US 11,655,218 B2
(45) Date of Patent: May 23, 2023

(54) CRYSTALLINE SUBSTITUTED PYRAZINES AS PGI2 RECEPTOR AGONISTS

(71) Applicant: NIPPON SHINYAKU CO., LTD., Kyoto (JP)

(72) Inventor: Toshio Fujiwara, Paramus, NJ (US)

(73) Assignee: NIPPON SHINYAKU CO., LTD., Kyoto (JP)

( * ) Notice: Subject to any disclaimer, the term of this patent is extended or adjusted under 35 U.S.C. 154(b) by 259 days.

(21) Appl. No.: 17/134,796

(22) Filed: Dec. 28, 2020

(65) Prior Publication Data

US 2021/0114995 A1  Apr. 22, 2021

Related U.S. Application Data

(62) Division of application No. 16/650,390, filed as application No. PCT/JP2018/035828 on Sep. 27, 2018, now Pat. No. 10,906,879.

(30) Foreign Application Priority Data

Sep. 28, 2017 (JP) .............................. JP2017-187296

(51) Int. Cl.
*C07D 241/26* (2006.01)
*C07D 241/20* (2006.01)

(52) U.S. Cl.
CPC ......... *C07D 241/20* (2013.01); *C07D 241/26* (2013.01); *C07B 2200/13* (2013.01)

(58) Field of Classification Search
CPC .................................................. C07D 241/26
See application file for complete search history.

(56) References Cited

U.S. PATENT DOCUMENTS

| 7,205,302 B2 | 4/2007 | Asaki et al. |
| 2004/0102436 A1 | 5/2004 | Asaki et al. |
| 2011/0015211 A1 | 1/2011 | Murakami et al. |
| 2011/0105518 A1 | 5/2011 | Kuwano |
| 2011/0118254 A1 | 5/2011 | Kyoi |
| 2011/0178103 A1 | 7/2011 | Matsuda et al. |
| 2012/0101276 A1 | 4/2012 | Itou et al. |
| 2014/0221397 A1 | 8/2014 | Murakami et al. |
| 2018/0029998 A1 | 2/2018 | Tang et al. |

FOREIGN PATENT DOCUMENTS

| CN | 106957269 A | 7/2017 |
| CN | 107365275 B | 7/2020 |
| EP | 1 400 518 A1 | 3/2004 |
| RU | 2283835 C2 | 9/2006 |
| RU | 2556206 C2 | 7/2015 |
| WO | 2002/088084 A1 | 11/2002 |
| WO | 2009/107736 A1 | 9/2009 |
| WO | 2009/154246 A1 | 12/2009 |
| WO | 2009/157396 A1 | 12/2009 |
| WO | 2009/157397 A1 | 12/2009 |
| WO | 2009/157398 A1 | 12/2009 |
| WO | 2010/150865 A1 | 12/2010 |
| WO | 2016/180033 A1 | 11/2016 |
| WO | 2017/042828 A2 | 3/2017 |
| WO | 2017/042828 A3 | 3/2017 |
| WO | 2018/008042 A1 | 1/2018 |

OTHER PUBLICATIONS

Dario Braga et al., "Crystal Polymorphism and Multiple Crystal Forms," Structure and Bonding, vol. 132, pp. 25-50, 2009.
Mino R. Caira, "Crystalline Polymorphism of Organic Compounds," Design of Organic Solids, Topics in Current Chemistry, vol. 198, Abstract only of pp. 163-208, 1998.
Rolf Hilfiker et al., "Relevance of Solid-state Properties for Pharmaceutical Products," Polymorphism: in the Pharmaceutical Industry, Chapter 1, pp. 1-19, 2006.
Instituto Mexicano de la Propiedad Industrial (IMPI), Official Action issued in Mexican Patent Application No. MX/a/2020/007315, which is a Mexican counterpart of U.S. Appl. No. 17/134,796, dated May 10, 2022, 8 pages (3 pages of English translation of Official Action and 5 pages of original Official Action).
European Patent Office, "Extended European Search Report," issued in European Patent Application No. 18 860 498.7, which is a European counterpart of U.S. Appl. No. 17/134,796, dated May 11, 2021, 8 pages.
European Patent Office, "Communication", issued in European Patent Application No. 18 860 498.7, which is a European counterpart of U.S. Appl. No. 17/134,796, dated Aug. 2, 2022, 6 pages.
Selexipag "Sele-Acid (SLAG-01)" Repetition of experiments reported in the prior art, Jun. 21, 2022, pp. 1-44, submitted by Dr. Schon, Neymeyr & Partner, to European Patent Office.
Tetsuo Asaki et al., "Selexipag: An Oral and Selective IP Prostacyclin Receptor Agonist for the Treatment of Pulmonary Arterial Hypertension," Journal of Medicinal Chemistry, vol. 58, pp. 7128-7137, 2015, American Chemical Society.
Intellectual Property India, Government of India, "Examination Report," issued in Indian Patent Application No. 202047013223, which is an Indian counterpart of U.S. Appl. No. 17/134,796, dated Jan. 4, 2022, 6 pages.
Tatsuya Atsumi et al., "Improvement of skin temperature of fingers by beraprost sodium in patients with Raynaud's phenomenon," Japanese Journal of Clinical Immunology, vol. 16, No. 5, 1993, pp. 409-414.

(Continued)

*Primary Examiner* — Brian E McDowell

(57) ABSTRACT

A main object of the present invention is to provide a novel crystal of 2-{4-[N-(5,6-diphenylpyrazin-2-yl)-N-isopropylamino]butyloxy}acetic acid (hereinafter referred to as "Compound B").
A form-I crystal of Compound B, which shows peaks at diffraction angles (2θ) of 6.4°, 8.1°, 9.5°, 10.9°, 13.2°, 15.7°, 17.0°, 19.5°, 20.3°, 21.0°, and 22.8° in a powder X-ray diffraction spectrum obtained using a Cu-Kα radiation (λ=1.54 Å).
A form-II crystal of Compound B, which shows peaks at diffraction angles (2θ) of 9.6°, 11.4°, 11.7°, 16.3°, 17.5°, 18.5°, 18.7°, 19.9°, 20.1°, 21.0°, and 24.6° in a powder X-ray diffraction spectrum obtained using a Cu-Kα radiation (λ=1.54 Å).

3 Claims, 9 Drawing Sheets

(56) References Cited

OTHER PUBLICATIONS

David B. Badesch et al., "Longterm Survival Among Patients with Scleroderma-associated Pulmonary Arterial Hypertension Treated with Intravenous Epoprostenol," The Journal of Rheumatolgy, vol. 36, No. 10, 2009, pp. 2244-2249, [online] <http://www.jrheum.org/>, retrieved Mar. 11, 2020.

G. Bergman et al., "Prostacyclin: Haemodynamic and Metabolic Effects in Patients with Coronary Artery Disease," The Lancet, vol. 317, No. 8220, Mar. 14, 1981, pp. 569-572, Elsevier B. V.

Yan Chen et al., "Protective Effect of Beraprost Sodium, a Stable Prostacyclin Analog, in the Development of Cigarette Smoke Extract-Induced Emphysema," American Journal of Physiology Lung Cellular and Molecular Physiology, vol. 296, 2009, pp. L648-L656, the American Physiological Society.

P. Henriksson et al., "Prostacyclin infusion in patients with acute myocardial infarction," British Heart Journal, vol. 53, Feb. 1985, pp. 173-179, [online] <https://heart.bmj.com/>, retrieved Mar. 12, 2020.

Tetsuya Hirano et al., "Effect of Beraprost Sodium (TRK-100) on Erythrocyte Deformability, Blood Viscosity and Thrombus Formation in Rats," Japanese Journal of Thrombosis and Hemostasis, vol. 1, No. 2, 1990, pp. 94-105.

Noriaki Hirayama, "Organic compound crystal production handbook—Principles and know-how—," Tokyo Maruzen Inc., Jul. 25, 2008, ISBN 978-4-621-07991-1, pp. 37-84.

Marco Idzko et al., "Inhaled iloprost suppresses the cardinal features of asthma via inhibition of airway dendritic cell function," The Journal of Clinical Investigation, vol. 117, No. 2, Feb. 2007, pp. 464-472.

T. Matsumoto et al., "The efficacy of Oral Beraprost Sodium, a prostaglandin I2 analogue, for treating intermittent claudication in patients with arteriosclerosis obliterans", International Angiology, vol. 29, Suppl. 1 to No. 2, Apr. 2010, pp. 49-54 Edizioni Minerva Medica.

Yoshinobu Nakai et al., "New formulation," Nanzandou Co., Ltd., Nov. 25, 1982, ISBN 4-525-77291-3, pp. 102-104 and pp. 217-236.

Shintaro Nishio et al., "Pharmacological and clinical properties of beraprost sodium, orally active prostacyclin analogue", Folia Pharmacologica Japonica, Feb. 2001, 117(2), pp. 123-130.

Yusaku Shioji, "Manufacture Technology of Solid Tablet," Tokyo: CMC Publishing Co., Ltd., Jan. 27, 2003, ISBN 4-88231-783-4, pp. 9-14.

Teruhiko Umetsu et al., "Antithrombotic Effect of TRK-100, a Novel, Stable PGI2 Analogue," The Japanese Journal of Pharmacology, vol. 43, 1987, pp. 81-90, The Japanese Pharmacological Society.

Masateru Yamada et al., "Amelioration by beraprost sodium, a prostacyclin analogue, of established renal dysfunction in rat glomerulonephritis model," European Journal of Pharmacology, vol. 449, 2002, pp. 167-176, Elsevier B.V.

Hao Yin et al., "Prostaglandin I2 and E2 Mediate the Protective Effects of Cyclooxygenase-2 in A Mouse Model of Immune-Mediated Liver Injury," Hepatology, vol. 45, No. 1, Jan. 2007, pp. 159-169, American Association for the Study of Liver Diseases.

United States Patent and Trademark Office, "Restriction Requirement," issued in U.S. Appl. No. 16/650,390, dated May 1, 2020, 5 pages.

United States Patent and Trademark Office, "Non-Final Office Action," issued in U.S. Appl. No. 16/650,390, dated Aug. 11, 2020, 10 pages.

Mino R. Caira, "Crystalline Polymorphism of Organic Compounds", Topics in Current Chemistry, vol. 198, pp. 163-208, 1998, Springer Verlag Berlin Heidelberg.

Sherry L. Morissette et al., "High-throughput crystallization: polymorphs, salts, co-crystals and solvates of pharmaceutical solids", Advanced Drug Delivery Reviews, vol. 56, pp. 275-300, 2004, Elsevier B.V.

Rospatent Federal Service on Intellectual Property, "Official Action", issued in Russian Patent Application No. 2020112117, which is a counterpart to U.S. Appl. No. 17/134,796, dated Oct. 3, 2022, 26 pages (13 pages of English translation of Official Action and 13 pages of original Official Action).

Narayan Variankaval et al., "From Form to Function: Crystallization of Active Pharmaceutical Ingredients", AIChE Journal, vol. 54, No. 7, pp. 1682-1688, Jul. 2008, American Institute of Chemical Engineers.

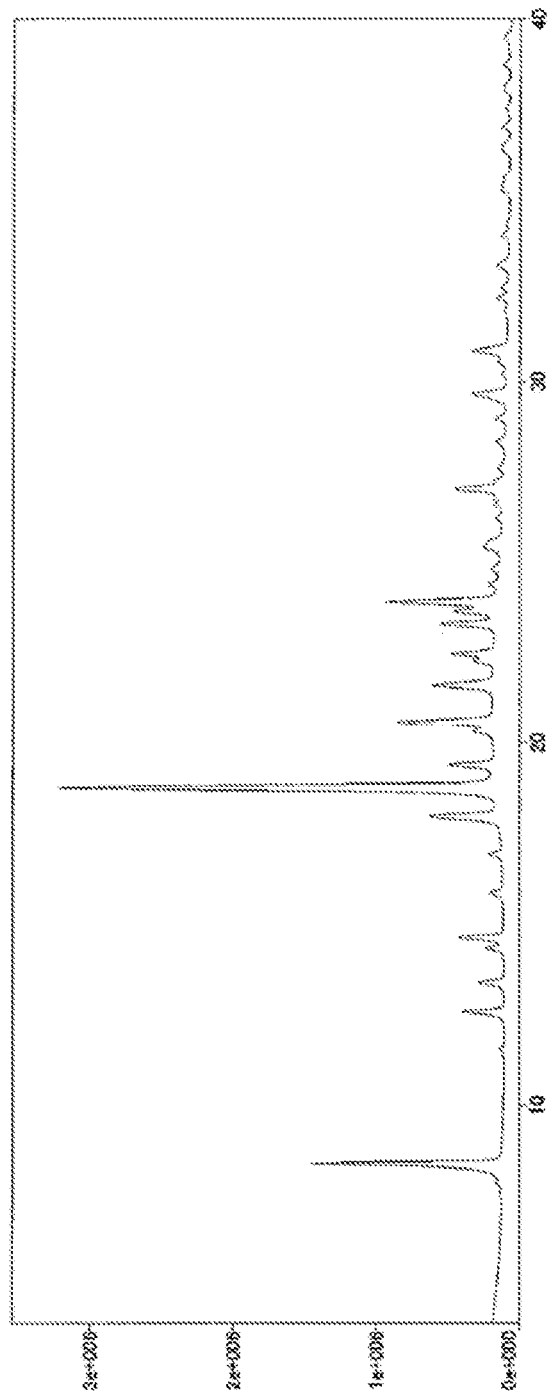
[FIG. 1]

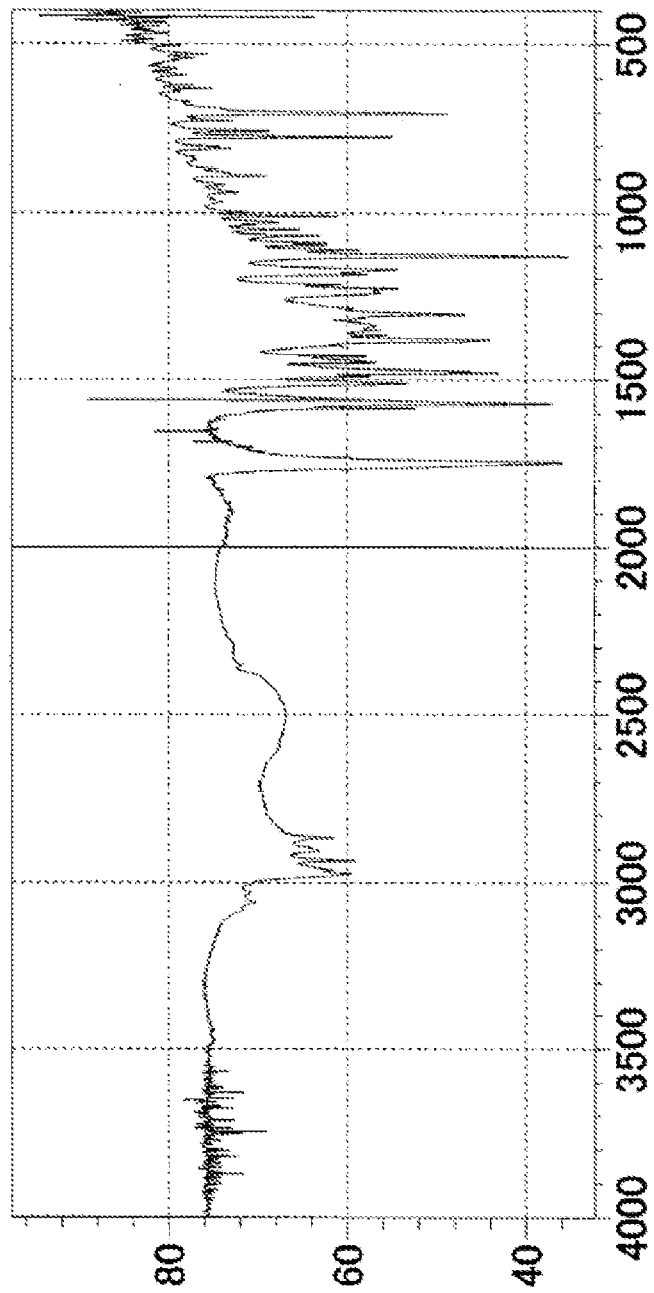
[FIG. 2]

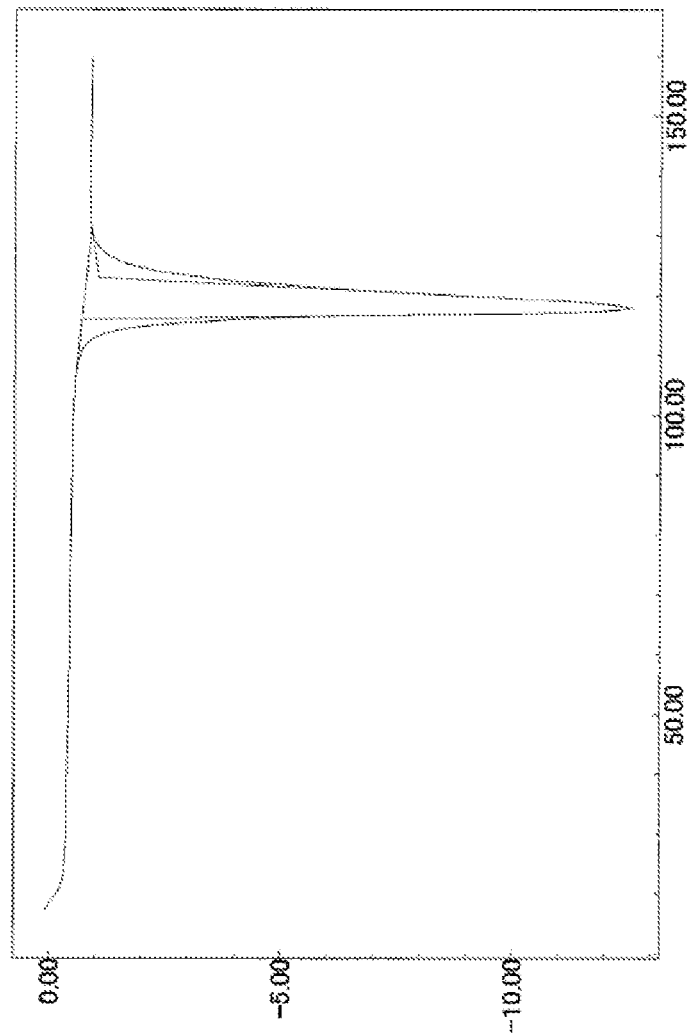
[FIG. 3]

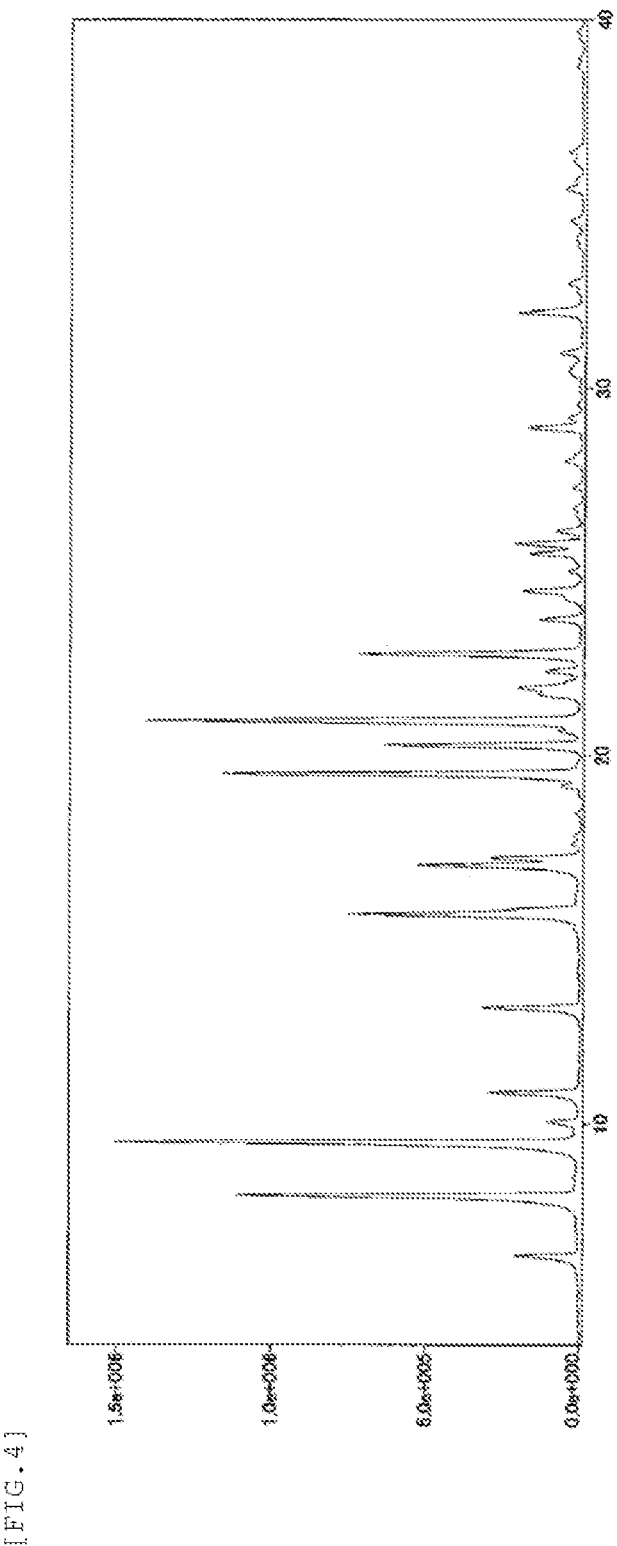
[FIG. 4]

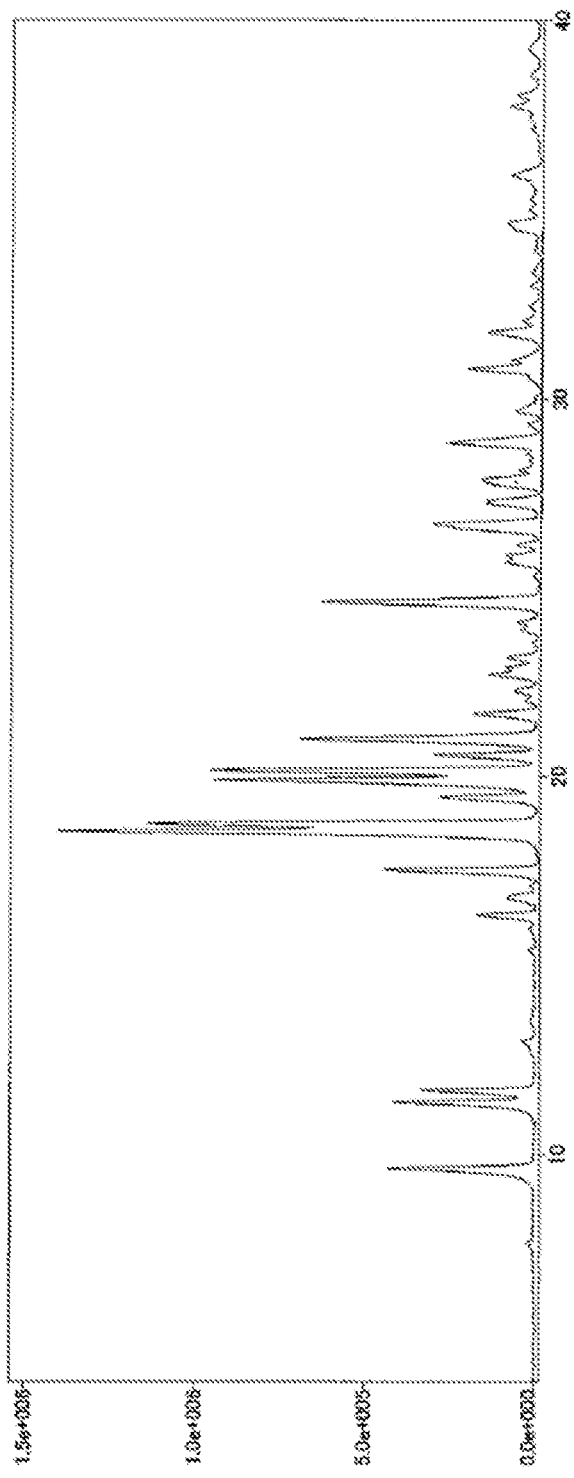
[FIG. 5]

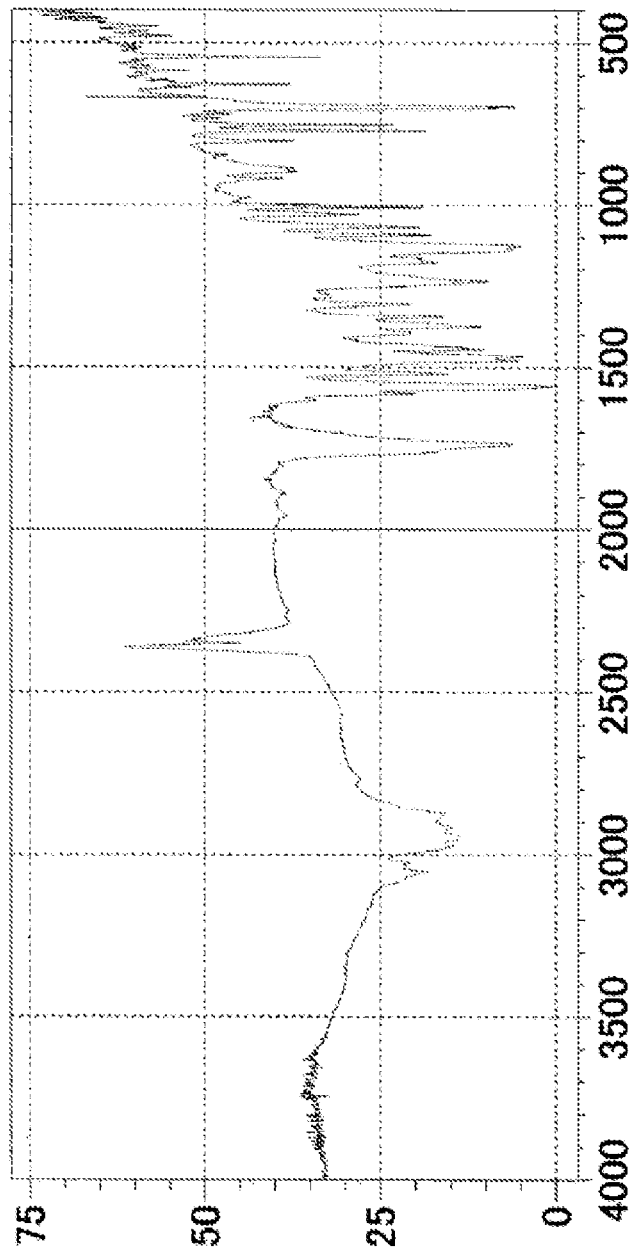
[FIG. 6]

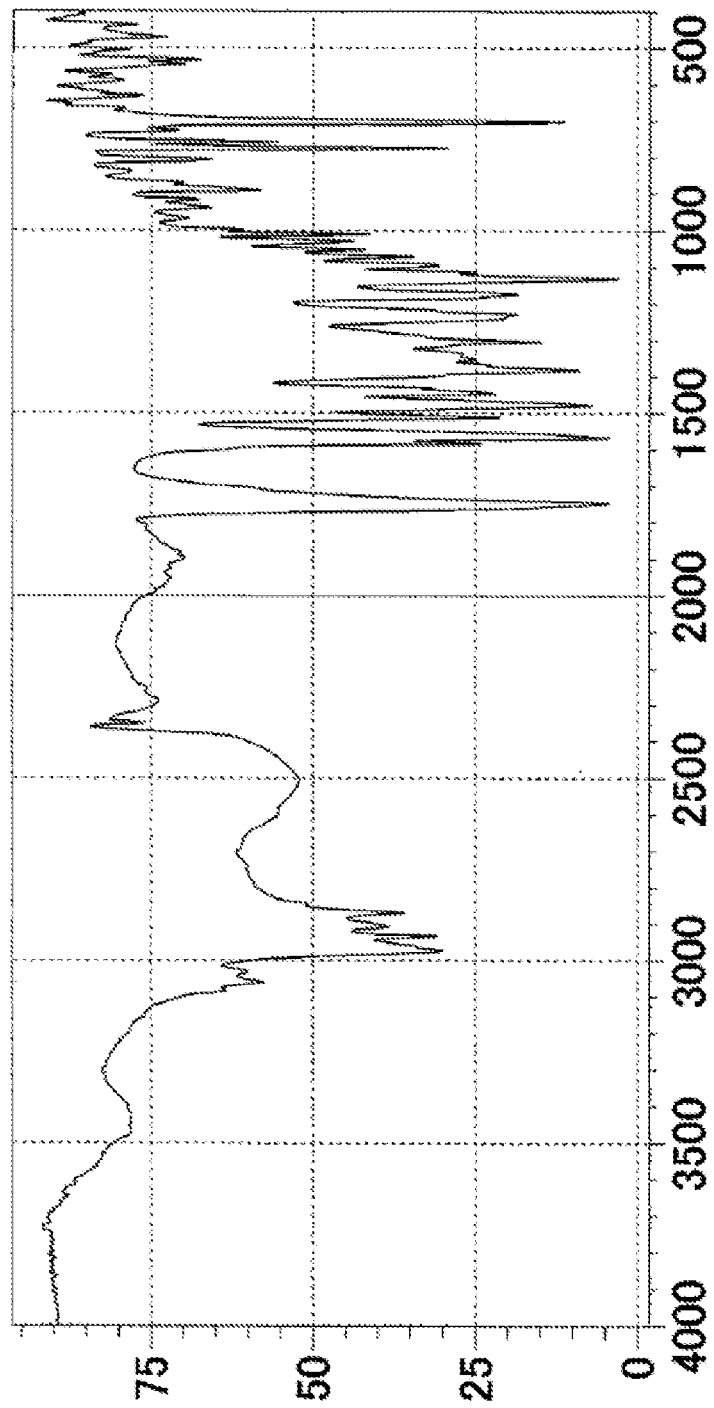
[FIG. 7]

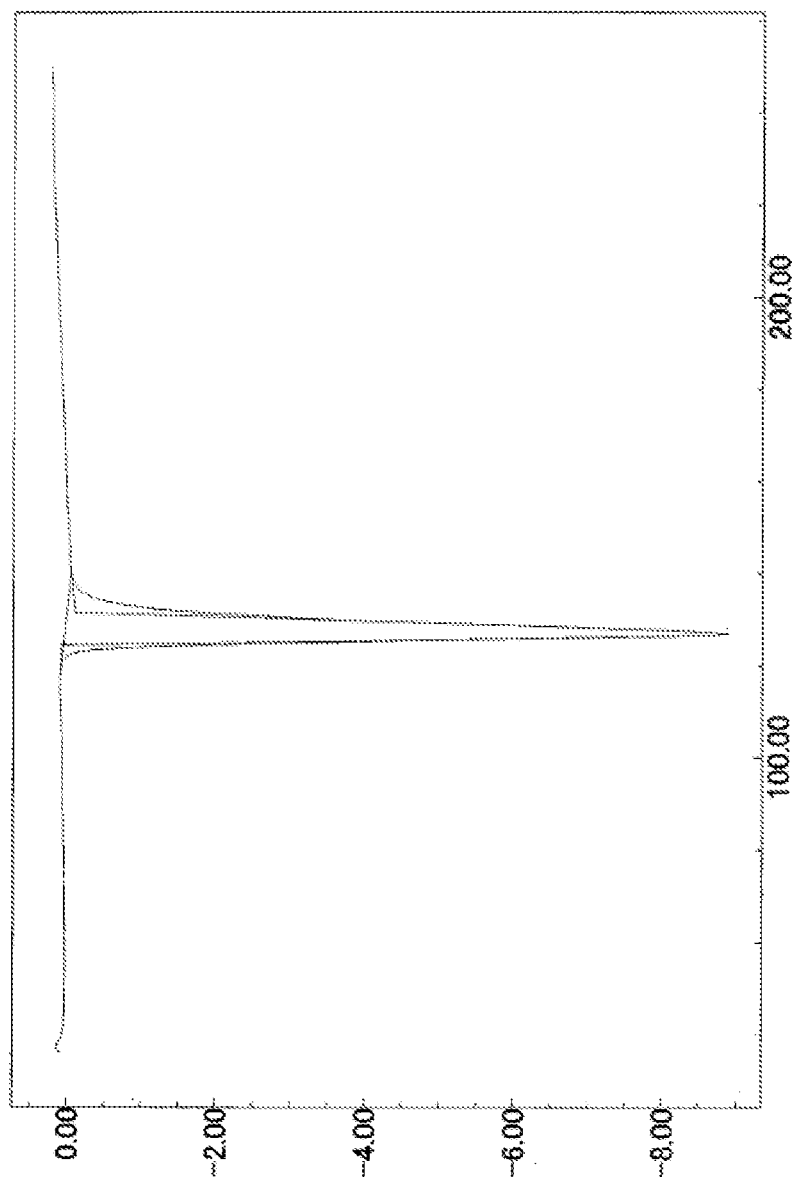
[FIG. 8]

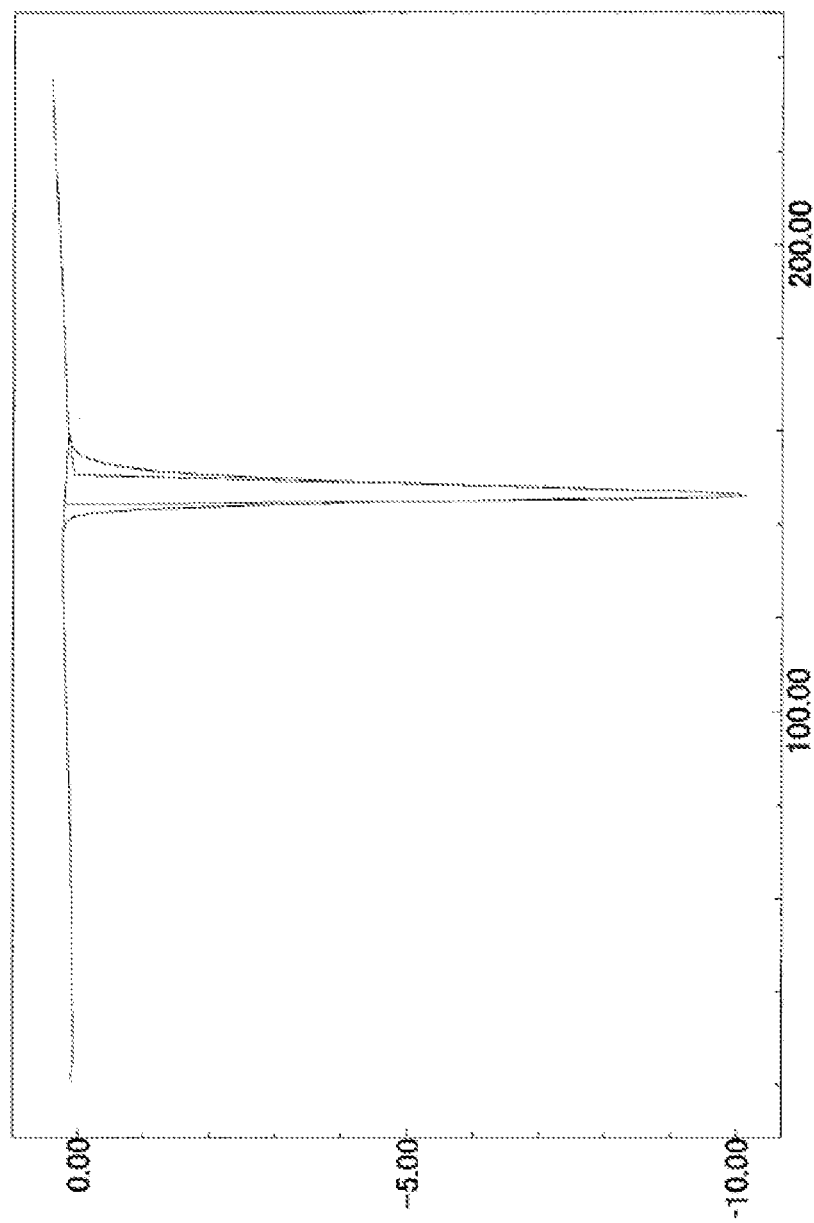
[FIG. 9]

CRYSTALLINE SUBSTITUTED PYRAZINES AS PGI2 RECEPTOR AGONISTS

CROSS REFERENCE TO RELATED APPLICATIONS

This patent application is a divisional of co-pending U.S. application Ser. No. 16/650,390 having a § 371(c) filing date of Mar. 25, 2020, which is a U.S. national stage application under 35 U.S.C. § 371 of International Patent Application No. PCT/JP2018/035828 filed on Sep. 27, 2018, which claims the benefit of foreign priority to Japanese Patent Application No. JP 2017-187296 filed on Sep. 28, 2017, the disclosures of all of which are hereby incorporated by reference in their entireties. The International Application was published in Japanese on Apr. 4, 2019, as International Publication No. WO 2019/065792 A1 under PCT Article 21(2).

TECHNICAL FIELD

The present invention relates to a novel crystal of 2-{4-[N-(5,6-diphenylpyrazin-2-yl)-N-isopropylamino]butyloxy}acetic acid (hereinafter referred to as "Compound B").

[Chem. 1]

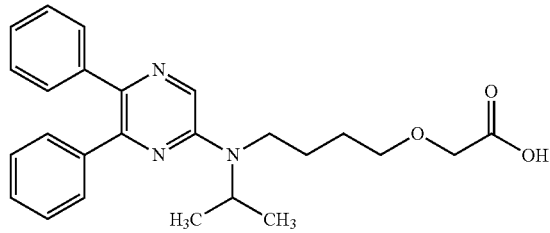

BACKGROUND ART

A pharmaceutical product is required to maintain its quality over a long period of time even under various conditions of distribution, storage, etc. Therefore, a compound to serve as an active ingredient is required to have high physicochemical stability. Due to this, as an active ingredient of a pharmaceutical product, a crystal which can be expected to have high stability is generally adopted.

In a process for screening a crystal of an active ingredient of a pharmaceutical product, not only is it difficult to find optimal conditions for obtaining the crystal, but also, even if the crystal is obtained, the existence of polymorphism is often problematic. The problem is caused because there is a difference in physicochemical stability depending on the crystal form.

Further, if the crystal form to be adopted as an active ingredient of a pharmaceutical product is erroneously selected, a decrease in purity, crystal form transformation, or the like occurs depending on the external environment during storage, and thus, it becomes difficult to maintain the quality of the compound constant, and therefore, depending on the crystal form, an unexpected event such as a decrease in drug efficacy or an adverse effect may be caused. Due to this, when a crystal of a compound to serve as an active ingredient of a pharmaceutical product is acquired successfully, it is necessary to perform strict evaluation and examination of the physicochemical stability of the polymorphism.

However, it is impossible to predict the existence or non-existence of polymorphism or a stable crystal form from the structure of a compound, and moreover, there exists a compound which cannot be crystallized in some cases, and it is necessary to variously study the conditions for forming a crystal for each compound.

On the other hand, Compound B is known to have an excellent PGI2 receptor agonistic effect and show various medicinal effects such as a platelet aggregation inhibitory effect, a vasodilating effect, a bronchial smooth muscle dilating effect, a lipid deposition inhibitory effect, and a leukocyte activation inhibitory effect (see, for example, PTL 1 to PTL 6). However, the current situation is that it is not known whether or not a crystal can be formed, much less whether or not polymorphism exists, and it is an important object to acquire an optimal crystal for development thereof as a pharmaceutical product.

CITATION LIST

Patent Literature

[PTL 1] WO 2002/088084
[PTL 2] WO 2009/157396
[PTL 3] WO 2009/107736
[PTL 4] WO 2009/154246
[PTL 5] WO 2009/157397
[PTL 6] WO 2009/157398
[PTL 7] US 2014/0221397
[PTL 8] US 2011/0178103
[PTL 9] US 2011/0015211
[PTL 10] US 2011/0118254
[PTL 11] US 2011/0105518

Non Patent Literature

[NPL 1] Hepatology, 2007, Vol. 45, No. 1, pp. 159-169
[NPL 2] PubMed: Nihon Yakurigaku Zasshi, 2001, February, 117(2), pp. 123-130, Abstract
[NPL 3] International Angiology, 29, Suppl. 1 to No. 2, pp. 49-54, 2010
[NPL 4] Japanese Journal of Clinical Immunology, Vol. 16, No. 5, pp. 409-414, 1993
[NPL 5] Japanese Journal of Thrombosis and Hemostasis, Vol. 1, No. 2, pp. 94-105, 1990, Abstract
[NPL 6] The Journal of Rheumatology, Vol. 36, No. 10, pp. 2244-2249, 2009
[NPL 7] The Japanese Journal of Pharmacology, Vol. 43, No. 1, pp. 81-90, 1987
[NPL 8] British Heart Journal, Vol. 53, No. 2, pp. 173-179, 1985
[NPL 9] The Lancet, 1, 4880, pt 1, pp. 569-572, 1981
[NPL 10] European Journal of Pharmacology, 449, pp. 167-176, 2002
[NPL 11] The Journal of Clinical Investigation, 117, pp. 464-72, 2007
[NPL 12] American Journal of Physiology Lung Cellular and Molecular Physiology, 296: L648-L656 2009

SUMMARY OF INVENTION

Technical Problem

An object of the present invention is to provide a crystal of Compound B having excellent physicochemical stability and also to provide a pharmaceutical composition containing the crystal as an active ingredient.

Solution to Problem

A method for producing Compound B is disclosed in Example 42 of PTL 1. However, in Example 42 of PTL 1, it is not specified what form of Compound B was obtained.

Therefore, when the present inventor made an attempt to produce Compound B according to the same procedure as the method disclosed in Example 42 of PTL 1, it was found that the form is a crystal (hereinafter referred to as "form-III crystal") (see the below-mentioned Reference Example 1). The results of powder X-ray diffraction measurement, IR measurement, and DSC measurement of the form-III crystal are shown in FIG. 1, FIG. 2, and FIG. 3, respectively.

However, as shown in the below-mentioned Test Example 1, it was found that the form-III crystal is thermodynamically unstable, and therefore, the present inventor made intensive studies in order to achieve the above object, and as a result, it was found that there exist a form-I crystal and a form-II crystal, each of which is thermodynamically more stable, and thus, the present invention was completed.

The present invention can include, for example, the following (1) to (7).

(1) A form-I crystal of Compound B (hereinafter referred to as "form-I crystal of the present invention"), which shows diffraction peaks at diffraction angles (2θ) of 6.4°, 8.1°, 9.5°, 10.9°, 13.2°, 15.7°, 17.0°, 19.5°, 20.3°, 21.0°, and 22.8° in a powder X-ray diffraction spectrum obtained using a Cu-Kα radiation ($\lambda$=1.54 Å).

(2) A form-I crystal of the present invention, which shows absorption peaks at wavenumbers of 2874 $cm^{-1}$, 1736 $cm^{-1}$, 1558 $cm^{-1}$, 1375 $cm^{-1}$, 1126 $cm^{-1}$, and 696 $cm^{-1}$ in an infrared absorption spectrum.

(3) A form-I crystal of the present invention, which has an endothermic peak at 127° C. in differential scanning calorimetry.

(4) A form-II crystal of Compound B (hereinafter referred to as "form-II crystal of the present invention"), which shows diffraction peaks at diffraction angles (2θ) of 9.6°, 11.4°, 11.7°, 16.3°, 17.5°, 18.5°, 18.7°, 19.9°, 20.1°, 21.0°, and 24.6° in a powder X-ray diffraction spectrum obtained using a Cu-Kα radiation ($\lambda$=1.54 Å).

(5) A form-II crystal of the present invention, which shows absorption peaks at wavenumbers of 2867 $cm^{-1}$, 1749 $cm^{-1}$, 1568 $cm^{-1}$, 1382 $cm^{-1}$, 1131 $cm^{-1}$, and 701 $cm^{-1}$ in an infrared absorption spectrum.

(6) A form-II crystal of the present invention, which has an endothermic peak at 147° C. in differential scanning calorimetry.

(7) A pharmaceutical composition containing the crystal according to any one of (1) to (6) as an active ingredient (hereinafter referred to as "pharmaceutical composition of the present invention").

When specifying a diffraction angle (2θ) for a diffraction peak in Examples and the claims of the present invention, it should be understood that an obtained value is within the range of the value ±0.2°, preferably within the range of the value ±0.1°.

Further, when specifying an absorption peak in an infrared absorption spectrum (hereinafter referred to as "IR spectrum") in Examples and the claims of the present invention, it should be understood that an obtained value is within the range of the value ±2 $cm^{-1}$, preferably within the range of the value ±1 $cm^{-1}$.

Further, when specifying an endothermic peak by a differential scanning calorimetry (hereinafter referred to as "DSC") in Examples and the claims of the present invention, it should be understood that an obtained value is within the range of the value ±3° C., preferably within the range of the value ±2° C.

BRIEF DESCRIPTION OF DRAWINGS

FIG. 1 shows a powder X-ray diffraction spectrum chart of a form-III crystal. The vertical axis represents a peak intensity (cps) and the horizontal axis represents a diffraction angle (2θ [°]).

FIG. 2 shows an IR spectrum chart of the form-III crystal. The vertical axis represents a transmittance (%) and the horizontal axis represents a wavenumber ($cm^{-1}$).

FIG. 3 shows a DSC measurement chart when the temperature of the form-III crystal was increased by 10° C. per minute. The vertical axis in the drawing represents an exothermic amount (mW) (in the case of a negative value, the value represents an endothermic amount) and the horizontal axis represents a temperature (° C.).

FIG. 4 shows a powder X-ray diffraction spectrum chart of the form-I crystal of the present invention. The vertical axis represents a peak intensity (cps) and the horizontal axis represents a diffraction angle (2θ [°]).

FIG. 5 shows a powder X-ray diffraction spectrum chart of the form-II crystal of the present invention. The vertical axis represents a peak intensity (cps) and the horizontal axis represents a diffraction angle (2θ [°]).

FIG. 6 shows an IR spectrum chart of the form-I crystal of the present invention. The vertical axis represents a transmittance (%) and the horizontal axis represents a wavenumber ($cm^{-1}$).

FIG. 7 shows an IR spectrum chart of the form-II crystal of the present invention. The vertical axis represents a transmittance (%) and the horizontal axis represents a wavenumber ($cm^{-1}$).

FIG. 8 shows a DSC measurement chart when the temperature of the form-I crystal of the present invention was increased by 10° C. per minute. The vertical axis represents an exothermic amount (mW) per second (in the case of a negative value, the value represents an endothermic amount) and the horizontal axis represents a temperature (° C.).

FIG. 9 shows a DSC measurement chart when the temperature of the form-II crystal of the present invention was increased by 10° C. per minute. The vertical axis in the drawing represents an exothermic amount (mW) (in the case of a negative value, the value represents an endothermic amount) and the horizontal axis represents a temperature (° C.).

DESCRIPTION OF EMBODIMENTS

A. Form-I Crystal of the Present Invention

The form-I crystal of the present invention is characterized in that it shows diffraction peaks at diffraction angles (2θ) of 6.4°, 8.1°, 9.5°, 10.9°, 13.2°, 15.7°, 17.0°, 19.5°, 20.3°, 21.0°, and 22.8° in a powder X-ray diffraction spectrum obtained using a Cu-Kα radiation ($\lambda$=1.54 Å). Further, it is preferably characterized in that it shows diffraction peaks at 15.8°, 17.2°, 21.9°, 23.7°, 24.5°, 25.5°, 25.8°, 28.9°, and 32.0° in addition to the above-mentioned diffraction peaks.

Further, the form-I crystal of the present invention is characterized in that it shows absorption peaks at wavenumbers of 2874 cm$^{-1}$, 1736 cm$^{-1}$, 1558 cm$^{-1}$, 1375 cm$^{-1}$, 1126 cm$^{-1}$, and 696 cm$^{-1}$ in an IR spectrum (KBr method).

Further, the form-I crystal of the present invention is characterized in that it has an endothermic peak at 127° C. in differential scanning calorimetry.

The form-I crystal of the present invention can be obtained by, for example, the method described in the below-mentioned Example 1.

B. Form-II Crystal of the Present Invention

The form-II crystal of the present invention is characterized in that it shows diffraction peaks at diffraction angles (2θ) of 9.6°, 11.4°, 11.7°, 16.3°, 17.5°, 18.5°, 18.7°, 19.9°, 20.1°, 21.0°, and 24.6° in a powder X-ray diffraction spectrum obtained using a Cu-Kα radiation (λ=1.54 Å). Further, it is preferably characterized in that it shows diffraction peaks at 19.4°, 20.6°, 21.1°, 21.7°, 22.7°, 26.6°, 26.7°, 28.8°, and 30.8° in addition to the above-mentioned diffraction peaks.

Further, the form-II crystal of the present invention is characterized in that it shows absorption peaks at wavenumbers of 2867 cm$^{-1}$, 1749 cm$^{-1}$, 1568 cm$^{-1}$, 1382 cm$^{-1}$, 1131 cm$^{-1}$, and 701 cm$^{-1}$ in an IR spectrum (KBr method).

Further, the form-II crystal of the present invention is characterized in that it has an endothermic peak at 147° C. in differential scanning calorimetry.

The form-II crystal of the present invention can be obtained by, for example, the method described in the below-mentioned Example 2.

C. Medical Application•Pharmaceutical Composition of the Present Invention

The Compound B according to the present invention has an excellent PGI2 receptor agonistic effect and shows various medicinal effects such as a platelet aggregation inhibitory effect, a vasodilating effect, a bronchial smooth muscle dilating effect, a lipid deposition inhibitory effect, and a leukocyte activation inhibitory effect (see, for example, PTL 1).

Therefore, the form-I crystal of the present invention, the form-II crystal of the present invention (hereinafter, collectively referred to as "crystal of the present invention"), or the pharmaceutical composition of the present invention is useful as a preventive agent or a therapeutic agent for transient ischemic attack (TIA), diabetic neuropathy (see, for example, NPL 1), diabetic gangrene (see, for example, NPL 1), a peripheral circulatory disturbance [for example, chronic arterial occlusion (see, for example, NPL 2), intermittent claudication (see, for example, NPL 3), peripheral embolism, vibration syndrome, or Raynaud's disease] (see, for example, NPL 4 and NPL 5), a connective tissue disease [for example, systemic lupus erythematosus, scleroderma (see, for example, PTL 7 and NPL 6), a mixed connective tissue disease, or a vasculitic syndrome], reocclusion/restenosis after percutaneous transluminal coronary angioplasty (PTCA), arteriosclerosis, thrombosis (for example, acute-phase cerebral thrombosis or pulmonary embolism) (see, for example, NPL 5 and NPL 7), hypertension, pulmonary hypertension, an ischemic disease [for example, cerebral infarction or myocardial infarction (see, for example, NPL 8)], angina pectoris (for example, stable angina pectoris or unstable angina pectoris) (see, for example, NPL 9), glomerulonephritis (see, for example, NPL 10), diabetic nephropathy (see, for example, NPL 1), chronic renal failure (see, for example, PTL 8), allergy, bronchial asthma (see, for example, NPL 11), ulcer, pressure ulcer (bedsore), restenosis after coronary intervention such as atherectomy or stent implantation, thrombocytopenia by dialysis, a disease in which fibrogenesis in an organ or a tissue is involved [for example, a renal disease {for example, tubulointerstitial nephritis (see, for example, PTL 9)}, a respiratory disease {for example, interstitial pneumonia (for example, pulmonary fibrosis) (see, for example, PTL 9), a chronic obstructive pulmonary disease (see, for example, NPL 12)}, a digestive disease (for example, hepatocirrhosis, viral hepatitis, chronic pancreatitis, or scirrhous gastric cancer), a cardiovascular disease (for example, myocardial fibrosis), a bone or articular disease (for example, bone marrow fibrosis or rheumatoid arthritis), a skin disease (for example, postoperative cicatrix, burn cicatrix, keloid, or hypertrophic cicatrix), an obstetric disease (for example, uterine fibroid), a urinary disease (for example, prostatic hypertrophy), other diseases (for example, Alzheimer's disease, sclerosing peritonitis, type I diabetes, and postoperative organ adhesion)], erectile dysfunction (for example, diabetic erectile dysfunction, psychogenic erectile dysfunction, psychotic erectile dysfunction, erectile dysfunction due to chronic renal failure, erectile dysfunction after pelvic operation for resection of the prostate, or vascular erectile dysfunction associated with aging or arteriosclerosis), an inflammatory bowel disease (for example, ulcerative colitis, Crohn's disease, intestinal tuberculosis, ischemic colitis, or intestinal ulcer associated with Behcet disease) (see, for example, PTL 10), gastritis, gastric ulcer, an ischemic eye disease (for example, retinal artery occlusion, retinal vein occlusion, or ischemic optic neuropathy), sudden hearing loss, avascular necrosis of bone, an intestinal damage caused by administration of a non-steroidal anti-inflammatory agent (NSAID) (for example, diclofenac, meloxicam, oxaprozin, nabumetone, indomethacin, ibuprofen, ketoprofen, naproxen, or celecoxib) (there is no particular limitation as long as it is a damage occurring in, for example, the duodenum, small intestine, or large intestine, however, for example, a mucosal damage such as erosion or ulcer occurring in the duodenum, small intestine, or large intestine), or symptoms (for example, paralysis, dullness in sensory perception, pain, numbness, or a decrease in walking ability) associated with spinal canal stenosis (for example, cervical spinal canal stenosis, thoracic spinal canal stenosis, lumbar spinal canal stenosis, coexisting cervical and lumbar spinal stenosis, or sacral spinal stenosis) (see PTL 11).

In addition, the crystal of the present invention or the pharmaceutical composition of the present invention is also useful as an accelerating agent for gene therapy or angiogenic therapy such as autologous bone marrow transplantation, or an accelerating agent for angiogenesis in restoration of peripheral artery or angiogenic therapy.

When the crystal of the present invention is administered as a pharmaceutical, the crystal is administered as it is, or is contained in a pharmaceutically acceptable nontoxic inert carrier in an amount within the range of, for example, 0.1% to 99.5%, preferably within the range of 0.5% to 90%.

Examples of the carrier include solid, semi-solid, or liquid diluents, fillers, and other auxiliary agents for pharmaceutical formulation. Among these, one type or two or more types can be used.

The pharmaceutical composition of the present invention may be in any form of preparations for oral administration such as a powder, a capsule, a tablet, a sugar-coated tablet, a granule, a powder preparation, a suspension, a liquid, a syrup, an elixir, and a troche, and parenteral preparations such as an injection and a suppository in a solid or liquid dosage unit. It may be in the form of a sustained release preparation. Among these, particularly, preparations for oral administration such as a tablet are preferred.

The powder can be produced by grinding the crystal of the present invention to an appropriate fineness.

The powder preparation can be produced by grinding the crystal of the present invention to an appropriate fineness, and then mixing the ground crystal with a similarly ground pharmaceutical carrier, for example, an edible carbohydrate such as starch or mannitol. A flavor, a preservative, a dispersant, a colorant, a perfume, or the like can be arbitrarily added thereto.

The capsule can be produced by firstly filling a powder or a powder preparation formed into a powdery shape as described above or a granulated material as will be described in the section on the tablet in, for example, a capsule shell such as a gelatin capsule. Further, the capsule can be produced by mixing a lubricant or a fluidizing agent such as colloidal silica, talc, magnesium stearate, calcium stearate, or solid polyethylene glycol with a powder or a powder preparation formed into a powdery shape, and thereafter performing a filling operation. It is possible to improve the effectiveness of the pharmaceutical when the capsule is taken if a disintegrating agent or a solubilizing agent such as carboxymethyl cellulose, carboxymethyl cellulose calcium, low-substituted hydroxypropyl cellulose, croscarmellose sodium, carboxymethyl starch sodium, calcium carbonate, or sodium carbonate is added thereto.

Further, it is also possible to form a soft capsule by suspending and dispersing the fine powder of the crystal of the present invention in a vegetable oil, polyethylene glycol, glycerin, or a surfactant, and wrapping the resulting material with a gelatin sheet.

The tablet can be produced by adding an excipient to the powdered crystal of the present invention to prepare a powder mixture, granulating or slagging the powder mixture, and then adding a disintegrating agent or a lubricant thereto, followed by tableting.

The powder mixture can be prepared by mixing the suitably powdered crystal of the present invention with a diluent or a base. If necessary, it is possible to add a binder (for example, carboxymethyl cellulose sodium, methyl cellulose, hydroxypropylmethyl cellulose, gelatin, polyvinylpyrrolidone, or polyvinyl alcohol), a dissolution retarding agent (for example, paraffin), a reabsorbing agent (for example, a quaternary salt), an adsorbent (for example, bentonite or kaolin), or the like thereto.

The granule can be produced by firstly wetting the powder mixture with a binder, for example, a syrup, a starch paste, gum Arabic, a cellulose solution, or a polymeric substance solution, stirring and mixing the wet mixture, and then, drying and crushing the mixture. In place of the granulation of the powder in this manner, it is also possible to form the granule by firstly subjecting the powder to a tableting machine, and thereafter crushing the slag as obtained in an incomplete shape. By adding stearic acid, a stearate salt, talc, a mineral oil, or the like as a lubricant to the thus produced granule, the granules can be prevented from adhering to each other.

Further, the tablet can also be produced by mixing the crystal of the present invention with a fluid inert carrier, and thereafter directly tableting the resulting mixture without undergoing a granulation or slagging step as described above.

The thus produced tablet can be subjected to film coating or sugar coating. It is also possible to use a transparent or semi-transparent protective coating film made of a shellac sealing coating film, a coating film made of a sugar or a polymeric material, or a polished coating film made of a wax.

Another preparation for oral administration, for example, a liquid, a syrup, a troche, or an elixir can also be formulated into a dosage unit form such that a predetermined amount thereof contains a predetermined amount of the crystal of the present invention.

The syrup can be produced by dissolving the crystal of the present invention in an appropriate aqueous flavor solution. The elixir can be produced using a non-toxic alcohol carrier.

The suspension can be produced by dispersing the crystal of the present invention in a non-toxic carrier. If necessary, it is possible to add a solubilizing agent or an emulsifier (for example, an ethoxylated isostearyl alcohol or a polyoxyethylene sorbitol ester), a preservative, a flavor-imparting agent (for example, peppermint oil or saccharine), or the like thereto.

If necessary, the dosage unit formulation for oral administration may be microencapsulated. It is also possible to extend the duration of action or achieve sustained release by coating the formulation or embedding the formulation in a polymer, a wax, or the like.

The preparation for parenteral administration may be in a liquid dosage unit form for subcutaneous, intramuscular or intravenous injection, for example, in the form of a solution or a suspension. The preparation for parenteral administration can be produced by suspending or dissolving a predetermined amount of the crystal of the present invention in a non-toxic liquid carrier meeting the purpose of injection, for example, an aqueous or oily medium, and then sterilizing the suspension or solution. It is also possible to add a stabilizing agent, a preservative, an emulsifier, or the like thereto.

The suppository can be produced by dissolving or suspending the crystal of the present invention in a solid which has a low melting point and is soluble or insoluble in water, for example, polyethylene glycol, cacao butter, a semi-synthetic oil or fat [for example, Witepsol (registered trade mark)], a higher ester (for example, myristyl palmitate ester), or a mixture thereof.

The dose varies depending on the state of a patient such as body weight or age, the administration route, the nature and severity of a disease, or the like, however, the dose as the amount of the crystal of the present invention per day per adult is suitably within the range of 0.001 mg to 100 mg, preferably within the range of 0.01 mg to 10 mg.

In some cases, a dose not more than the above range may be sufficient, or on the other hand, a dose not less than the above range may be needed. Further, the preparation can be administered once to several times a day or can be administered with an interval of one to several days.

EXAMPLES

Hereinafter, the present invention will be described in more detail with reference to Examples and Test Examples, however, the present invention is by no means limited thereto.

A powder X-ray diffraction spectrum was measured using SmartLab (manufactured by Rigaku Corporation) (optical system: focusing method, voltage: 45 kV, current: 200 mA, wavelength: Cu-K$\alpha$, solar slit: 5.0°, scan range: 4 to 40°, scan speed: 47.3°/min, sample rotation: 60°/min).

An IR spectrum was measured using IR Affinity-1 (manufactured by Shimadzu Corporation) (measurement mode: % Transmittance, cumulative number: 16 times, resolution: 2.0, wavenumber range: 400 to 4000 cm$^{-1}$).

A DSC was measured using DSC-50 (manufactured by Shimadzu Corporation) (cell: alumina (open), gas: nitrogen (20.0 mL/min), heating rate: 10° C./min, holding temperature: 250° C., holding time: 0 min).

Reference Example 1: Production of form-III Crystal

After tert-butyl 2-{4-[N-(5,6-diphenylpyrazin-2-yl)-N-isopropylamino]butyloxy}acetate (see, for example, PTL 1) (13.15 g) was dissolved in methanol (179.7 mL), a 1 N aqueous sodium hydroxide solution (41.47 mL) was added thereto. After the resulting mixture was heated under reflux for 1 hour, the solvent was distilled off under reduced pressure, and water was added to the residue to dissolve the residue. After washing was performed with diethyl ether, the obtained aqueous layer was neutralized with 1 N hydrochloric acid (44 mL), and extraction was performed with ethyl acetate. The obtained ethyl acetate layer was dried over anhydrous magnesium sulfate, and the solvent was distilled off under reduced pressure, and then, diisopropyl ether was added to the residue to effect crystallization. The resulting crystal was filtered and washed with an appropriate amount of diisopropyl ether. The crystal was dried at 40° C. under reduced pressure, whereby a form-III crystal (9.88 g) was obtained.

The results of powder X-ray diffraction measurement, IR measurement, and DSC measurement of the form-III crystal are shown in FIG. 1, FIG. 2, and FIG. 3, respectively.

diffraction angles (2θ): 8.4°, 12.6°, 13.4°, 14.3°, 14.6°, 15.9°, 16.9°, 18.0°, 18.8°, 19.4°, 20.3°, 20.6°, 21.6°, 21.7°, 22.3°, 22.5°, 23.3°, 23.7°, 23.9°, 27.0°, 29.6°, and 30.8°

IR absorption peaks: 2867 $cm^{-1}$, 1747 $cm^{-1}$, 1558 $cm^{-1}$, 1380 $cm^{-1}$, 1131 $cm^{-1}$, and 701 $cm^{-1}$ DSC endothermic peak: 118° C.

Reference Example 2: Production of Compound B

To a suspension of 2-{4-[N-(5,6-diphenylpyrazin-2-yl)-N-isopropylamino]butyloxy}-N-(methylsulfonyl)acetamide (see, for example, PTL 1) (300 g) in isopropyl alcohol (1425 mL), an aqueous sodium hydroxide solution (a solution obtained by dissolving sodium hydroxide (120.8 g) in water (570 mL)) was added. After stirring was performed at 100° C. for 11 hours, the resulting mixture was cooled to 10° C. or lower. After concentrated hydrochloric acid was added dropwise thereto, stirring was performed at 10° C. or lower for 1 hour, the resulting precipitate was filtered and washed with an appropriate amount of a 50% aqueous isopropyl alcohol solution, water, and acetonitrile. The precipitate was dried at 65° C. under reduced pressure, whereby a target compound (208.3 g) was obtained.

Example 1: Production of form-I Crystal of the Present Invention

Compound B (63 g) produced in Reference Example 2 was dissolved in acetonitrile (315 mL) at 90° C., and stirring was performed at the same temperature for 30 minutes. The solution was filtered, and washing was performed with 5 mL of acetonitrile, and stirring with heating was performed again. As stimulation, a small amount of Compound B produced in Reference Example 2 was added thereto, followed by gradual cooling, and stirring was performed at 10° C. or lower for 1 hour, and then, the crystal was filtered and washed with an appropriate amount of acetonitrile. The crystal was dried at 65° C. under reduced pressure, whereby the form-I crystal of the present invention (59.5 g) was obtained.

The results of powder X-ray diffraction measurement, IR measurement, and DSC measurement of the form-I crystal of the present invention are shown in FIG. 4, FIG. 6, and FIG. 8, respectively.

diffraction angles (2θ): 6.4°, 8.1°, 9.5°, 10.9°, 13.2°, 15.7°, 15.8°, 17.0°, 17.2°, 19.5°, 20.3°, 21.0°, 21.9°, 22.8°, 23.7°, 24.5°, 25.5°, 25.8°, 28.9°, and 32.0°

IR absorption peaks: 2874 $cm^{-1}$, 1736 $cm^{-1}$, 1558 $cm^{-1}$, 1375 $cm^{-1}$, 1126 $cm^{-1}$, and 696 $cm^{-1}$ DSC endothermic peak: 127° C.

Example 2: Production of form-II Crystal of the Present Invention

Compound B (0.5 g) produced in Reference Example 2 was dissolved in isopropyl alcohol (2.5 mL) and an 8% aqueous sodium hydroxide solution (1.5 mL) at 80° C., and stirring was performed at the same temperature for 30 minutes. The solution was gradually cooled to room temperature, and the pH of the solution was adjusted to 5 to 6 with a 4 N aqueous hydrochloric acid solution at room temperature, and then, stirring was performed at 10° C. or lower for 1 hour. Thereafter, the crystal was filtered and washed with an appropriate amount of water. The crystal was dried at 65° C. under reduced pressure, whereby the form-II crystal of the present invention (0.45 g) was obtained.

The results of powder X-ray diffraction measurement, IR measurement, and DSC measurement of the form-II crystal of the present invention are shown in FIG. 5, FIG. 7, and FIG. 9, respectively.

diffraction angles (2θ): 9.6°, 11.4°, 11.7°, 16.3°, 17.5°, 18.5°, 18.7°, 19.4°, 19.9°, 20.1°, 20.6°, 21.0°, 21.1°, 21.7°, 22.7°, 24.6°, 26.6°, 26.7°, 28.8°, and 30.8°

IR absorption peaks: 2867 $cm^{-1}$, 1749 $cm^{-1}$, 1568 $cm^{-1}$, 1382 $cm^{-1}$, 1131 $cm^{-1}$, and 701 $cm^{-1}$ DSC endothermic peak: 147° C.

Test Example 1: Stability Test

Different crystal forms of Compound B were placed in glass bottles, respectively, and the glass bottles were hermetically sealed and stored at 90° C. Samples were taken out after 1 day, 5 days, and 14 days, and dissolved in methanol at a concentration of 1 mg/mL to determine related substances by HPLC. With respect to the crystals after 14 days, the crystal form was checked. The results are shown in Table 1.

TABLE 1

| | Form-I | | Form-II | | Form-III | |
|---|---|---|---|---|---|---|
| Storage conditions | Appearance | HPLC area (%) | Appearance | HPLC area (%) | Appearance | HPLC area (%) |
| Before storage | White crystal | 99.8 | Yellow crystal | 100 | Yellow crystal | 99.9 |
| 90° C., after 1 day | No change | 99.8 | No change | 100 | No change | 99.9 |
| 90° C., after 5 days | No change | 99.8 | No change | 100 | No change | 99.9 |
| 90° C., after 14 days | No change | 99.6 | No change | 99.9 | No change | 99.7 |
| Crystal form after 14 days | Form-I + Form-II | | Form-II | | Form-II | |

From the above results, it was revealed that in any of the crystal forms, chemical stability is very high, however, the form-I and the form-III are gradually transformed into the form-II which is thermodynamically stable.

Test Example 2: Solvent Suspending Test of Form-I Crystal of the Present Invention in Different Solvents The form-I crystal of the present invention was mixed with different solvents, and stirring was performed at room temperature for 30 minutes. The formed crystals were obtained by filtration, and the crystal forms were determined. The results are shown in Table 2.

TABLE 2

| Solvent | Crystal form after 30 minutes at room temperature |
| --- | --- |
| cyclohexane | Form-I + Form-II (1:1) |
| water | Form-I + Form-II (10:1) |
| 2-propanol | Form-I + Form-II (1:10) |
| toluene | Form-I + Form-II (10:1) |

As described above, the form-I crystal of the present invention was partially transformed into the form-II crystal of the present invention when suspended in all the solvents. From these results, it was revealed that the form-II crystal of the present invention is thermodynamically stable when suspended in various solvents at room temperature.

The invention claimed is:

1. A form-I crystal of 2-{4-[N-(5,6-diphenylpyrazin-2-yl)-N-isopropylamino]butyloxy}acetic acid, which shows diffraction peaks at diffraction angles (2θ) of 6.4°, 8.1°, 9.5°, 10.9°, 13.2°, 15.7°, 17.0°, 19.5°, 20.3°, 21.0°, and 22.8° in a powder X-ray diffraction spectrum obtained using a Cu-Kα radiation (λ=1.54 Å).

2. The form-I crystal of 2-{4-[N-(5,6-diphenylpyrazin-2-yl)-N-isopropylamino]butyloxy}acetic acid according to claim 1, which shows absorption peaks at wavenumbers of 2874 $cm^{-1}$, 1736 $cm^{-1}$, 1558 $cm^{-1}$, 1375 $cm^{-1}$, 1126 $cm^{-1}$, and 696 $cm^{-1}$ in an infrared absorption spectrum.

3. The form-I crystal of 2-{4-[N-(5,6-diphenylpyrazin-2-yl)-N-isopropylamino]butyloxy}acetic acid according to claim 1, which has an endothermic peak at 127° C. in differential scanning calorimetry.

* * * * *